United States Patent [19]  [11]  4,315,918
Gayst et al.  [45]  Feb. 16, 1982

[54] PHARMACEUTICAL FORMULATION OF GUAR GUM

[76] Inventors: Stephen Gayst, 19 Arthur St., Double Bay, N.S.W., Australia, 2028; Michael J. Maguire, 9 Cotton St., Epping, N.S.W., Australia, 2121

[21] Appl. No.: 66,304

[22] Filed: Aug. 13, 1979

[30] Foreign Application Priority Data

Jul. 25, 1978 [GB] United Kingdom ............... 31060/78

[51] Int. Cl.³ ..................... A61K 37/02; A61K 31/73; C07H 37/00
[52] U.S. Cl. ................................ 424/177; 260/112 R; 424/180; 536/114
[58] Field of Search ................... 536/114, 1; 424/180; 427/177; 260/112 R

[56] References Cited

U.S. PATENT DOCUMENTS

| | | | |
|---|---|---|---|
| 3,313,800 | 4/1967 | Jackson, Jr. et al. | 536/1 |
| 3,330,706 | 7/1967 | Griffith | 149/38 |
| 3,360,511 | 12/1967 | Farkas | 424/180 |
| 3,362,951 | 1/1968 | Farkas et al. | 424/180 |
| 3,396,034 | 8/1968 | Blondheim et al. | 536/114 |
| 3,415,927 | 10/1968 | Butensky et al. | 536/114 |
| 3,712,883 | 1/1973 | Nordgren | 536/114 |
| 3,989,683 | 11/1976 | Staba | 536/114 |
| 4,098,859 | 7/1978 | Cummisford et al. | 536/114 |
| 4,175,124 | 11/1979 | Hyldon et al. | 424/180 |

*Primary Examiner*—Johnnie R. Brown
*Attorney, Agent, or Firm*—Donald Brown

[57] ABSTRACT

The gellation of polysaccharide gums such as guar or locust bean gum is inhibited by gelatin hydrolysates, at alkaline pH. Formulations of gum, gelatin hydrolysate and alkaliniser are reconstituted by shaking with water, and are easily imbibed. The inhibition is reversed by pH change in the stomach allowing gellation to occur. The formulation is useful in treatment of hypercholesteraemia, gastric disorders and as an adjunct to insulin therapy.

23 Claims, No Drawings

PHARMACEUTICAL FORMULATION OF GUAR GUM

This invention relates to formulations of polysaccharide gums, notably guar gum and locust bean gum, wherein the gellation of the gum is inhibited or retarded until after entry into the stomach.

Polysaccharide gums are natural products extracted from various plants, in particular from the leguminose, such as *Cyamopsis tetragonolobus* (guar) and *Ceratonia siliqua* L (locust bean or carob) [R. L. Whistler, Industrial Gums, 2nd Edition, Academic Press, N.Y. and London, 1973; F. Smith and R. Montgomery, The Chemistry of Plant Gums and Mucilages, Reinhold Publishing Corp., New York, 1959]. Medical uses of these gums include treatment of gastro-intestinal disorders [Cummins, Lancet (1975), 5] and hypercholesteraemia [Jenkins, Lancet, (1976), 1351] and as an adjunct to insulin treatment of diabetes [Jenkins, Lancet, (1977), 779].

The therapeutic effect of polysaccharide gums is apparently related to their ability to form viscous gels in aqueous solution due to interparticulate forces between polysaccharide molecules at adjacent particle surfaces. When produced in the stomach such gels may entrap and thereby inhibit or alter absorption of glucose, cholesterol and, possibly, drugs.

The formation of such viscous gels is a problem in administration of polysaccharide gums to human patients. If taken in drinking water, a solution of greater than about 0.5% w/w polysaccharide gum is difficult to drink yet an excessively large volume of a more dilute solution is required. Polysaccharide gums may be administered in dry forms, such as baked in biscuits or bread. However these are rather inaccurate dosage forms and as typically only about 10% by weight of polysaccharide flour may be included in such products, as inconveniently large quantity must be ingested to achieve a suitable daily dose. Furthermore the baking process can damage and render ineffective, the polysaccharide gum. Alternatively the polysaccharide gum may be sprinkled on food, but it then imparts a slippery, gummy texture which is not acceptable to human patients.

The problem has been alleviated by heat treatment (U.S. Pat. No. 3,415,927), or surface treatment with chemicals (U.S. Pat. No. 3,330,706) which slow the rate of gellation to some extent, although the polysaccharide gum still hydrates sufficiently quickly that solutions must be imbibed immediately. Some chemical treatments require the use of toxic chemicals, such as borates, and are not suitable for use in preparing medical products. Heat treatment can degrade the polymer backbone of the polysaccharide gum to the extent that it can no longer form viscous gels.

It has now been found that certain water soluble macromolecular compounds inhibit or retard the gellation of colloidal solutions of polysaccharide gums and that this inhibition may nevertheless be advantageously reversed after the polysaccharide gum has passed into the stomach and gut.

According to the present invention, therefore, there is provided a formulation of a therapeutically useful polysaccharide gum, as hereinbefore defined, presented as a dry powder, suitable for reconstitution by admixture with drinking water for oral administration as a draught, wherein the polysaccharide gum is presented in admixture with an effective gellation-inhibiting quantity of a substantially linear, natural or modified natural macromolecular compound which is capable of inhibiting the gellation of polysaccharide gum solutions at a pH at which said compound is substantially neutral or negatively charged and having a solubility in water of at least 1% w/w at 15° C.

The term "polysaccharide gum" as used herein is intended to refer to materials composed of long chain polymers of one or more hexoses such as galactose or mannose having very short branches, each branch typically, but not exclusively, consisting of a single hexose residue. When dried or precipitated from solution such polysaccharide gums may be readily redissolved, and form stable, highly viscous solutions Embraced within the term "polysaccharide gums" are the galactomannans, that is, linear D-mannose polymers bearing D-galactose residues as side chains, such as guar gum in which every second D-mannose unit bears a D-galactose moiety and locust bean gum wherein the D-galactose residues occur on approximately every fourth D-mannose unit.

A therapeutically useful polysaccharide gum is one which is capable of forming sufficiently viscous gels. A convenient test of this ability is to prepare a 1% w/w solution of the gum in water and allow this to stand for 24 hours at 25° C., at which time the viscosity of a therapeutically useful polysaccharide gum is from 2 to $6 \times 10^3$ mPa s.

Many grades and forms of polysaccharide gums are commercially available, particularly of the galactomannans, guar gum and locust bean gum. Some of these are however unsuitable for therapeutic use having been treated chemically or thermally because they cannot form sufficiently viscous gels as described above. For the purposes of the present invention, therapeutically useful galactomannans are preferred, guar gum and locust bean gum being most preferred.

Macromolecular compounds as defined above are herein referred to as inhibitors. An "effective gellation-inhibiting quantity" of such an inhibitor is that amount which is sufficient to substantially prevent gellation of the reconstituted formulation for a prolonged period, preferably at least 15 minutes and more preferably 30 minutes or longer.

In order that inhibition should be quickly established before gellation of the guar gum occurs it is convenient to have an inhibitor that is soluble at at least about 1% w/w in cold, (15° C.) water, preferably about 5% w/w or more and most preferably about 10% w/w or greater.

For the reconstituted formulation to be drinkable the suspension should have a viscosity not exceeding about $1.5 \times 10^3$ mPa s, preferably below about $1 \times 10^3$ mPa s and most preferably less than about $0.5 \times 10^3$ mPa s. The major contribution to such viscosity is due to the polysaccharide gum, however, depending upon the chain length of the inhibitor, the latter may also contribute to the viscosity. Accordingly the mean chain length of the inhibitor is limited to an upper size commensurate with a drinkable reconstituted formulation. When the chain length is small, the inhibitor is less effective and inordinately large quantities of inhibitor may be required. Thus the chain length of the inhibitor is preferably selected such that the reconstituted formulation has an acceptable viscosity while the quantity of inhibitor required is relatively low.

The inhibition of gellation is believed to occur when the polysaccharide gum is first hydrated. The surface of the polysaccharide gum particles rapidly hydrate and associate either by hydrogen bonding or by electrostatic forces with the inhibitor, which has dissolved already. The hydrogen bonding between polysaccharide molecules, which would otherwise cause gellation, is impeded by the presence of the inhibitor. Thus a suspension of the formulation remains mobile for a prolonged period when sufficient inhibitor is present.

Inhibition can be reversed in the stomach by pH change, by dilution due to the stomach contents and by degradation of the inhibitor by gastric enzymes. Further degradation occurs in the gut due to pancreatic enzymes. It is preferred that inhibition should be reversible by pH change and most preferably by a combination of all three mechanisms.

Reversal of inhibition by dilution will apply to some extent to all inhibitors. Proteinaceous inhibitors are preferred, as they are also susceptible to degradation by gastric enzymes.

In order that reversal of inhibition should occur by pH change it is essential that the charge borne by the inhibitor should be pH dependant, such that at high pH's the inhibitor is negatively charged, while at acid pH's, as found in the stomach, the inhibitor is neutral or preferably positively charged.

Inhibitors which conform to the criteria of solubility and molecular weight given above, with the required pH charge dependence, are for instance hydrolysates of gelatin, other selected protein hydrolysates, carbohydrates and their derivatives, such as hydroxypropylmethylcellulose phthalate. Protein hydrolysates are particularly convenient, being susceptible to pH change, dilution and enzymatic degradation to reverse inhibition. Bovine and porcine gelation hydrolysates are preferred, those having a number mean molecular weight (by chromatography) of less than $5 \times 10^4$ having sufficiently low viscosity while hydrolysates having mean molecular weight above about $1 \times 10^4$ are effective in suitably low quantities. Bovine or porcine gelatin hydrolysates with a number mean molecular weight of about $3 \times 10^4$ (by chromatography) are particularly preferred.

Conveniently the ratio of inhibitor to polysaccharide gum in the formulation is from 0.5:1 to 6:1 by weight, preferably from 0.5 to 1 to 3:1 and most preferably from 0.5:1 to 1:5 to 1.

Inhibition is more effectively established in alkaline or slightly acid media and accordingly an alkaliniser may be included in the formulation to adjust the pH of the reconstituted formulation to a suitable value.

Accordingly there is provided in a second aspect of the invention, a formulation as hereinbefore defined also comprising an effective adjusting quantity of alkaliniser.

As used herein the term "alkaliniser" is intended to refer to a pharmaceutically acceptable water soluble compound capable of raising the pH of the reconstituted formulation to a value in the range of from pH 5 to pH 10.5. Accordingly an "effective adjusting quantity" of an alkaliniser is that quantity of an alkaliniser which is sufficient to bring the pH of the reconstituted formulation to the chosen pH. Suitable alkalinisers include sodium glycinate, calcium hydroxide or trisodium orthophosphate dodecahydrate. Sodium glycinate and calcium hydroxide are preferred.

The relative quantities of polysaccharide gum, inhibitor and alkaliniser incorporated in the formulation depend on the volume of liquid in which the formulation is to be reconstituted, the amount of polysaccharide gum to be administered and the chosen pH of the formulation.

More dilute suspensions of polysaccharide gum require relatively larger quantities of inhibitor than more concentrated suspensions. Thus the ratio of inhibitor to polysaccharide can be in the range from 0.5:1 to 6:1 by weight as hereinbefore described. However, at higher pH's relatively less inhibitor is required for a given concentration of polysaccharide gums than at lower pH's, and correspondingly a larger quantity of alkaliniser may be required to afford the higher pH.

The polysaccharide gum and/or the inhibitor may have a buffering effect on the reconstituted formulation, thereby increasing the amount of alkaliniser required to establish a particular pH. For this reason and because inhibition is more easily reversed in the stomach when there is less inhibitor present, it is preferred that the inhibitor to polysaccharide ratio is low and that the formulation has a high pH, preferably from pH 7.5 to pH 10.5.

Typical formulations of the present invention comprise either guar or locust bean gum in association with bovine or porcine gelatin hydrolysates of mean molecular weight $3 \times 10^4$ as inhibitor, and these are preferred.

The most preferred formulations of locust bean gum have an inhibitor to gum ratio of 0.5:1 by weight and include as alkaliniser, calcium hydroxide which is present at 7.5 to 10 mg per g of locust bean gum, preferably about 8.5 mg per g of locust bean gum.

The most preferred formulations of guar gum have an inhibitor to gum ratio of 2:1 to about pH 8 or 1.5:1 at about pH 10 and include as alkaliniser, sodium glycinate present at 20 to 40 mg per g of guar gum, preferably about 30 mg per g of guar gum or calcium hydroxide present at 30 to 50 mg per g, preferably about 40 mg per g of guar gum.

The formulation may also comprise pharmaceutically acceptable excipients, flavourings, sweeteners and surfactants. It is preferred that the polysaccharide gum and inhibitor have similar particle sizes thereby preventing separation on reconstitution. They are conveniently presented in unit dose form such as sachets of powder.

Formulations of the present invention are conveniently reconstituted for consumption using 10 to 25, preferably 15 to 20, especially about 17 cm$^3$ water per g of polysaccharide gum. Typically a sachet would contain 5 to 15 g of polysaccharide gum, especially about 10 g, and would therefore be reconstituted with 75 to 300 cm$^3$ water, preferably 150 to 200 cm$^3$ water.

According to the present invention in a third aspect there is provided a method of inhibiting the gellation of polysaccharide gum solutions comprising the addition of an affective inhibitory quantity of an inhibitor and an effective adjusting quantity of alkaliniser either simultaneously or prior to the addition of water to the polysaccharide gum.

According to the present invention in a further aspect there is provided a process for producing a formulation of polysaccharide gum comprising admixing the polysaccharide gum with at least an effective inhibitory quantity of an inhibitor and an effective adjusting quantity of an alkaliniser.

According to the present invention in a yet further aspect there is provided a method for treating humans or animals comprising the administration of a therapeutic dose of a polysaccharide gum in association with an effective inhibitory quantity of an inhibitor and an effective adjusting quantity of an alkaliniser.

Therapeutic doses of polysaccharide gums for humans are typically from 5 to 30 g per day. The formulations of the present invention may be administered several times per day to achieve the required therapeutic dose.

The invention will now be illustrated with reference to the following Examples, which are not intended to limit the scope of the invention in any way.

In these Examples Omprem 18 and MP 128 are Registered Trade Marks for guar gum and locust bean gum respectively, distributed by Davis Germantown (Australia) Pty Ltd. Croda Protein "S" is a Registered Trade Mark for Bovine gelatin hydrolysate typically having a mean molecular weight $3 \times 10^4$ manufactured and distributed by Croda Chemicals.

EXAMPLE 1

Formulations of 10 g guar gum and varying proportions of inhibitor were reconstituted in a volume of 160 cm³ at pH 8: a quantity of alkaliniser equivalent to 130 mg sodium hydroxide was required to achieve this pH. The viscosity was measured after 20 minutes using a Brookfield viscometer, spindle 5 at 20 r.p.m.

| Inhibitor: Guar gum ratio | Viscosity mPa s | Drinkable |
|---|---|---|
| 1.2:1 | 7500 | No |
| 1.5:1 | 1500 | Yes |
| 2:1 | 300 | Yes |

Accordingly a preferred formulation of guar gum was made by standard methods of pharmacy and placed in sachets, each of which contained the following ingredients:

| Guar gum (Omprem 18) | 10 g |
|---|---|
| Croda Protein "S" | 20 g |
| Sodium glycinate | 0.3 g |
| Flavouring | q.s. |

The formulation was reconstituted by sprinkling the contents of one sachet onto 160 ml tap water at 25° C. and shaking in a sealed container for 20 to 30 seconds. The reconstituted formulation had a pH of about 7.5. It remained drinkable for at least 2 hours.

The ingestion of such a formulation was simulated by pouring into 400 cm³ of pH 4 buffer at 37° C. The viscosity increased exponentially for the first 15 minutes and it was very viscous after 45 minutes.

EXAMPLE 2

Formulations of 8 g guar gum and varying proportions of inhibitor were reconstituted in a volume of 170 cm³ at pH 9.8: a quantity of alkaliniser equivalent to 300 mg of sodium hydroxide was required to achieve this pH.

Accordingly a preferred formulation of guar gum was made by standard methods of pharmacy and placed in sachets, each of which contained the following ingredients:

| Guar gum (Omprem 18) | 8 g |
|---|---|
| Croda Protein "S" | 12 g |
| Calcium hydroxide | 0.32 g |
| Flavouring | q.s. |

The formulation was reconstituted by sprinkling the contents of one sachet onto 170 ml tap water at 22° C. and shaking in a sealed container for 5 to 10 seconds. The reconstituted formulation had a pH of about 9.8. It remained drinkable for at least 10 minutes.

The ingestion of such a formulation was simulated by pouring into 400 cm³ of pH 6 buffer at 37° C. The viscosity increased exponentially for the first 15 minutes and it was very viscous after 30 minutes.

EXAMPLE 3

Formulations of 8 g locust bean gum and varying proportions of inhibitor were reconstituted in a volume of 170 cm³ at pH 9.8: a quantity of alkaliniser equivalent to 70 mg sodium hydroxide was required to achieve this pH.

Accordingly a preferred formulation of locust bean gum was made by standard methods of pharmacy and placed in sachets, each of which contained the following ingredients:

| Locust bean gum (MP 128) | 8 g |
|---|---|
| Croda Protein "S" | 4 g |
| Calcium hydroxide | 0.07 g |
| Flavouring | q.s. |

The formulation was reconstituted by sprinkling the contents of one sachet onto 170 ml tap water at 22° C. and shaking in a sealed container for 5 to 15 seconds. The reconstituted formulation had a pH of about 9.8. It remained drinkable for at least 10 minutes.

The ingestion of such a formulation was simulated by pouring into 400 cm³ of an acidic solution with a reconstituted pH of 2.5. The viscosity increased rapidly for the first 15 minutes and was very viscous after 45 minutes.

EXAMPLE 4

Volunteers were fasted for 11 to 12 hours then fed with a standard meal comprising:

| Cornflakes | 20 g |
|---|---|
| White bread | 60 g (toasted if requested) |
| Butter | q.s. |
| Unsweetened pineapple juice | 150 ml |
| Milk | 300 ml |
| Honey | 20 g | which was eaten in the same order, over a period of 10 minutes. Five minutes after the start of the meal guar gum was administered in the following formulation:

| Guar gum | 8 g |
|---|---|
| Croda Protein "S" | 12 g |
| Flavouring | q.s. |
| alkaliniser | 7.5 m Eq of NaOH | which was reconstituted by shaking in 150 ml of water. Each volunteer also took a similar meal without guar gum to act as control. Plasma glucose levels were determined every half hour after the start of the meal. Results were presented in Table 1.

Table 1

Plasma glucose levels (mM) in volunteers at half hourly intervals after ingestions of a meal with or without guar gum.

| Volunteer No. | Time (hours) | | | | | |
|---|---|---|---|---|---|---|
| | 0 | 0.5 | 1 | 1.5 | 2 | 3 |
| 1 control | 4.9 | 6.1 | 5.9 | 5.0 | 4.6 | 4.4 |
| guar | 5 | 5.4 | 4.5 | 5.6 | 4.8 | 4.8 |
| 2 control | 5.5 | 7.1 | 6.1 | 6.1 | 5.3 | 4.7 |
| guar | 5.1 | 7.1 | 5.6 | 6.0 | 5.1 | 3.8 |
| 3 control | 4.7 | 7.0 | 5.1 | 5.1 | 5.4 | 5.0 |
| guar | 4.7 | 5.9 | 4.4 | 4.9 | 4.7 | 4.7 |
| 4 control | 5.0 | 6.1 | 3.7 | 4.4 | 4.7 | 4.9 |
| guar | 4.7 | 4.3 | 3.1 | 4.5 | 5.5 | 4.9 |
| 5 control | 4.4 | 6.1 | 5.6 | 5.2 | 5.6 | 4.5 |
| guar | 4.6 | 5.1 | 4.4 | 4.1 | 5.2 | 5.2 |
| 6 control | 5.0 | 6.5 | 3.9 | 3.7 | 4.9 | 3.7 |
| guar | 4.4 | 4.3 | 4.2 | 3.9 | 3.7 | 4.6 |

We claim:

1. A pharmaceutical composition for use in medicine, presented as a dry powder suitable for reconstitution by admixture with drinking water, said composition comprising a therapeutically effective, non-toxic amount of a galactomannan admixed with a gellation inhibiting amount of gelatin hydrolysate.

2. A composition as claimed in claim 1 which also comprises an effective adjusting quantity of an alkaliniser.

3. A composition as claimed in claim 2 wherein the alkaliniser is selected from sodium glycinate, calcium hydroxide or tri-sodium orthophosphate dodecahydrate.

4. A composition as claimed in claim 2 wherein the quantity of alkaliniser is sufficient to provide, in the reconstituted formulation, a pH in the range of from pH 5.0 to pH 10.5.

5. A composition as claimed in claim 4 wherein the quantity of alkaliniser is sufficient to provide, in the reconstituted formulation, a pH in the range from pH 8 to pH 10.

6. A composition as claimed in claim 1 wherein the galactomannan is either guar gum or locust bean gum.

7. A composition as claimed in claim 1 wherein the gelatin hydrolysate is a bovine or porcine gelatin hydrolysate.

8. A composition as claimed in claim 1 wherein the gelatin hydrolysate has a number mean molecular weight of from $1 \times 10^4$ to $5 \times 10^4$.

9. A composition as claimed in claim 8 wherein the gelatin hydrolysate has a number mean molecular weight of about $3 \times 10^4$.

10. A formulation as claimed in any one of claims 1–5, 6, or 7–9 wherein the gelatin hydrolysate to galactomannan ratio is from 0.5:1 to 6:1 by weight.

11. A composition as claimed in claim 10 wherein the gelatin hydrolysate to galactomannan ratio is from 0.5:1 to 3:1 by weight.

12. A composition as claimed in claim 11 wherein the gelatin hydrolysate to galactomannan ratio is from 0.5:1 to 1.5:1 by weight.

13. A composition as claimed in claim 2 wherein the galactomannan is locust bean gum and the alkaliniser is calcium hydroxide, the latter being present at from 7.5 to 10 mg/g of locust bean gum.

14. A composition as claimed in claim 13 wherein the calcium hydroxide is present at about 8.5 mg/g of locust bean gum.

15. A composition as claimed in any one of claims 1–5, 6, or 7–9 which comprises from 5 to 15 g of locust bean gum in unit dose form.

16. A composition as claimed in claim 15 which comprises about 10 g of locust bean gum in unit dose form.

17. A composition as claimed in any one of claims 2 to 5, 6 or 7–9 wherein the galactomannan is guar gum and the alkaliniser is sodium glycinate, the latter being present at from 20 to 40 mg/g of guar gum.

18. A composition as claimed in claim 17 wherein the sodium glycinate is present at about 30 mg/g of guar gum.

19. A composition as claimed in any one of claims 2 to 5, 6 or 7–9 wherein the galactomannan is guar gum and the alkaliniser is calcium hydroxide, the latter being present at from 30 to 50 mg/g of guar gum.

20. A composition as claimed in claim 19 wherein the calcium hydroxide is present at about 40 mg/g of guar gum.

21. A composition as claimed in claim 1 which comprises from 5 to 15 g of guar gum in unit dose form.

22. A composition as claimed in claim 21 which comprises about 10 g of guar gum in unit dose form.

23. A method for inhibiting the gellation of a galactomannan solution, said method comprising the admixture of gelatin hydrolysate and an alkalinizer either simultaneously with or prior to the addition of water to the galactomannan.

* * * * *